United States Patent [19]

Reid et al.

[11] Patent Number: 5,085,857
[45] Date of Patent: Feb. 4, 1992

[54] CONDITIONING SHAMPOO COMPRISING A SURFACTANT, A NON-VOLATILE SILICONE OIL AND GUAR HYDROXYPROPYLTRIMONIUM CHLORIDE AS A CATIONIC CONDITIONING POLYMER

[75] Inventors: Euan S. Reid, Bebington; Andrew M. Murray, Parkgate, both of Great Britain

[73] Assignee: Chesebrough-Pond's USA Co., Greenwich, Conn.

[21] Appl. No.: 621,482

[22] Filed: Dec. 3, 1990

[30] Foreign Application Priority Data

Dec. 4, 1989 [GB] United Kingdom ............ 8927385.8
Jul. 23, 1990 [GB] United Kingdom ............ 9016101.9

[51] Int. Cl.$^5$ .......................... A61K 7/06; A61K 7/75
[52] U.S. Cl. ..................................... 424/70; 424/496; 424/500; 514/881; 514/937; 514/938
[58] Field of Search ................. 424/70; 514/881, 941, 514/942, 937

[56] References Cited

U.S. PATENT DOCUMENTS

| 4,364,837 | 12/1982 | Pader | 252/173 |
| 4,559,227 | 12/1985 | Chandra et al. | 424/78 |
| 4,741,855 | 5/1988 | Grote et al. | 252/174.15 |
| 4,874,547 | 10/1989 | Narula | 514/941 |
| 4,933,176 | 6/1990 | Van Reeth | 514/788 |

FOREIGN PATENT DOCUMENTS 0018717 11/1980 European Pat. Off.
0035899 9/1981 European Pat. Off.

OTHER PUBLICATIONS

Hunting's "Encyclopaedia of Conditioning Rinse Ingredients", pp. 46-47.

Primary Examiner—Thurman K. Page
Assistant Examiner—David Colucci
Attorney, Agent, or Firm—Honig, Milton L.

[57] ABSTRACT

A shampoo composition contains surfactant together with a cationic derivative of guar gum and an insoluble non-volatile silicone present as emulsified particles having average particle size below 2μm. The silicone is preferably incorporated as a pre-formed emulsion.

10 Claims, No Drawings

CONDITIONING SHAMPOO COMPRISING A SURFACTANT, A NON-VOLATILE SILICONE OIL AND GUAR HYDROXYPROPYLTRIMONIUM CHLORIDE AS A CATIONIC CONDITIONING POLYMER

BACKGROUND OF THE INVENTION

The present invention relates to shampoo compositions, and more particularly to shampoo compositions containing non-volatile silicone materials which condition the hair leaving it softer and more manageable.

When washing the hair with conventional shampoo compositions, the natural oils are removed together with the dirt and unwanted oils. When too much of the natural oil is removed, for example by especially frequent washing, the hair becomes less easy to comb or style, and subject to static build-up causing "flyaway".

Hair conditioners have been developed to try to restore the condition of the hair. These compositions are normally applied to hair after shampooing, left on the hair for a period of time and rinsed off. This process is time consuming and expensive since two separate products are needed.

Conditioning shampoos containing cationic conditioning agents have been disclosed for example in EP 18 717 (Unilever). These cationic agents confer some conditioning benefit on the hair, but are often thought to leave a residue on the hair, which may cause dulling on hair after drying.

Non-volatile silicone oils are useful as conditioning agents, but again excessive amounts of silicone can dull the hair, and build-up of silicone on the hair can give a greasy appearance. Furthermore, the incorporation of silicone oil generally gives an antifoam effect.

Hair conditioning emulsions are disclosed in EP 35 899 (Proctor & Gamble). These emulsions comprise volatile silicone or volatile hydrocarbon, and the particle size of the volatile material in the final composition is said to be from 1 to 10 μm.

However, such compositions are not suitable for use as shampoos, and the hair should first be washed before applying the conditioner emulsion.

Non-volatile silicone oil has been incorporated directly into shampoo compositions, as disclosed in EP 74 264 (Unilever), however the silicone oil is incorporated directly into the compositions, giving a particle size larger than 2 μm, and an antifoam effect can be seen.

We have found that the combination of an aqueous emulsion of a silicone oil with a particular type of cationic conditioning polymer in a surfactant-based shampoo composition will impart improved conditioning benefit to the hair with none of the undesirable dulling effects or greasy build-up seen with other conditioning products, and without the need for a two-step washing and conditioning procedure.

Incorporating the silicone oil as a preformed aqueous emulsion has the consequences that the silicone is incorporated with a small particle size, less than 2 μm. The silicone is insoluble and remains emulsified in the overall composition. Incorporating the silicone oil in this way makes the manufacture of the compositions easier. It also reduces the antifoam action of the silicone oil and leads to compositions of greater stability.

Accordingly, the invention provides an aqueous shampoo composition comprising, in addition to water (a) from 2 to 40% by weight of surfactant chosen from anionic, nonionic or amphoteric surfactants or mixtures thereof;
(b) from 0.01 to 3% by weight of cationic conditioning polymer which is a cationic derivative of guar gum;
(c) from 0.01 to 10% by weight of an insoluble, non-volatile silicone, present as emulsified particles with an average particle size of less than 2 μm.

In another aspect, this invention provides a method of making such a shampoo composition, by mixing together water, the surfactant, the cationic conditioning polymer and an aqueous emulsion of the silicone, wherein the silicone in the emulsion has an average particle size of less than 2 μm.

DETAILED DESCRIPTION OF THE INVENTION

(a) Surfactant

The composition according to the invention comprises a surfactant chosen from anionic, nonionic or amphoteric surfactant or mixtures thereof.

Suitable anionic surfactants are the alkyl sulphates, alkyl ether sulphates, alkaryl sulphonates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl groups generally containing from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate and sodium N-lauryl sarcosinate. The most preferred anionic surfactant are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

The nonionic surfactants suitable for use in the composition of the invention may include condensation products of aliphatic ($C_8$-$C_{18}$) primary or secondary linear or branched chain alcohols or phenols with alkylene oxides, usually ethylene oxide and generally 6-30 EO.

Other suitable nonionics include mono or di alkyl alkanolamides or alkyl polyglucosides. Examples include coco mono or diethanolamide, coco mono isopropanolamide, and coco di glucoside.

The amphoteric surfactants suitable for use in the composition of the invention may include alkyl amine oxides, alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates and acyl glutamates wherein the alkyl and acyl groups have from 8 to 18 carbon atoms. Examples include lauryl amine oxide, cocodimethyl sulphopropyl betaine and preferably lauryl betaine, cocamidopropyl betaine and sodium cocamphopropionate.

The surfactants are present in the shampoo composition of the invention in an amount of from 2 to 40% by weight, and preferably from 5 to 30% by weight.

(b) Cationic conditioning polymer

The composition of the invention comprises a cationic conditioning polymer which is a cationic derivative of a guar gum.

Suitable cationic guar gum derivatives are those given the CTFA designation guar hydroxypropyl trimonium chloride, available commercially for example as JAGUAR C13S, which has a low degree of substitution of the cationic groups and a high viscosity. The low degree of cationic substitution leads to a cationic charge density of 0.0008. Other suitable materials include that known as JAGUAR C15, having a moderate degree of substitution and a low viscosity, JAGUAR C17 (high degree of substitution, hence cationic charge density of 0.0016, high viscosity) and JAGUAR C16 which is a hydroxypropylated cationic guar derivative containing a low level of substituent groups as well as cationic quaternary ammonium groups. JAGUAR C16 has a cationic charge density of 0.0008. Also suitable is JAGUAR 162 which is a high transparency, medium viscosity guar having a low degree of substitution.

The compositions of the invention contain from 0.01 to 3% by weight of cationic conditioning polymer, preferably from 0.1 to 2% by weight.

(c) Silicone

The shampoo composition of the invention also comprises an insoluble, non-volatile silicone, which may be one or more polyalkyl siloxanes, one or more polyalkylaryl siloxanes, or mixtures thereof. The silicone is insoluble in the aqueous matrix of the composition and so is present in an emulsified form, with the silicone present as dispersed particles.

Suitable polyalkyl siloxanes include polydimethyl siloxanes which have the CTFA designation dimethicone, having a viscosity of from 5 to 100,000 centistokes at 25° C. These siloxanes are available commercially from the General Electric Company as the Viscasil series and from Dow Corning as the DC 200 series. The viscosity can be measured by means of a glass capillary viscometer as set out further in Dow Corning Corporate Test Method CTM004 July 20, 1970.

Also suitable is polydiethyl siloxane.

The polyalkylaryl siloxanes which may be used in the compositions of the invention include polymethylphenyl polysiloxanes having a viscosity of from 15 to 65 centistokes at 25° C. These siloxanes are available commercially from the General Electric Company as SF 1075 methyl phenyl fluid or from Dow Corning as 556 Cosmetic Grade Fluid.

Also suitable are silicone gums, such as those described in U.S. Pat. No. 4,152,416 (Spitzer), and on General Electric Silicone Rubber product Data Sheet SE 30, SE 33, SE 54 and SE 76. "Silicone gum" denotes polydiorganosiloxanes having a molecular weight of from 200,000 to 1,000,000, and specific examples include polydimethyl siloxane polymer, polydimethyl siloxane/diphenyl/methylvinylsiloxane copolymer, polydimethylsiloxane/methylvinylsiloxane copolymer and mixtures thereof.

Aminofunctional silicones which have the CTFA designation amodimethicone, such as Union Carbide TP 407 are also suitable for use in the compositions of the invention.

The silicone materials described above are preferably incorporated in the shampoo composition of the invention as a pre-formed aqueous emulsion. The average particle size of the silicone material in this emulsion and in the shampoo composition is less than 2 $\mu$m, preferably from 0.01 to 1 $\mu$m. Particle size may be measured by means of a laser light scattering technique, using a 2600D Particle Sizer from Malvern Instruments.

The emulsion may be prepared by high shear mechanical mixing of the silicone and water, or by emulsifying the insoluble, non-volatile silicone with water and an emulsifier—mixing the silicone into a heated solution of the emulsifier for instance, or by a combination of mechanical and chemical emulsification.

Any surfactant materials either alone or in admixture may be used as emulsifiers in the preparation of the silicone emulsions. Preferred emulsifiers include anionic emulsifiers such as alkylarylsulphonates, e.g. sodium dodecylbenzene sulphonate, alkyl sulphates e.g. sodium, lauryl sulphate, alkyl ether sulphates e.g. sodium lauryl ether sulphate nEO, where n is from 1 to 20 alkylphenol ether sulphates e.g. octylphenol ether sulphate nEO where n is from 1 to 20, and sulphocuccinates e.g. sodium dioctylsulphosuccinate.

Also suitable are nonionic emulsifiers such as alkylphenol ethoxylates e.g. nonylphenol ethoxylate nEO, where n is from 1 to 50, alcohol ethoxylates e.g. lauryl alcohol nEO, where n is from 1 to 50, ester ethoxylates e.g. polyoxyethylene monostearate where the number of oxyethylene units is from 1 to 30.

Typically, a pre-formed emulsion will contain around 50% of silicone. Pre-formed emulsions are available from suppliers of silicone oils such as Dow Corning, General Electric, Union Carbide, Wacker Chemie, Shin Etsu, Toshiba, Toyo Beauty Co. and Toray Silicone Co.

The compositions of the invention contain from 0.01 to 10% by weight, preferably from 0.1 to 5% by weight, of insoluble, non-volatile silicone. If less than 0.01% by weight is present in the composition, little conditioning benefit is observed, and if more than 10% by weight is present, the hair will appear greasy.

The aqueous pre-formed emulsion may be incorporated into the shampoo composition in an amount of from 0.02 to 50% by weight, preferably from 0.2 to 20% by weight.

The exact quantity of emulsion will of course depend on the concentration of the emulsion, and should be selected to give the desired quantity of insoluble, non-volatile silicone, in the final composition.

To enhance stability, compositions of this invention preferably contain either a shear thinning polymer, such as a cross linked polyacrylate, or an insoluble solid which forms a network within the composition. Ethylene glycol distearate is such a solid: it also acts as a pearlescent agent.

USE OF THE COMPOSITION

The shampoo composition of the invention may be applied in an amount of from 3 to 5 ml to wet hair. The wet hair is worked to create a lather. The lather may be retained on the head for a short time before rinsing e.g. from 1 to 4 minutes, or may immediately be rinsed. The washing procedure may be repeated if required.

The hair is generally found to be clean, manageable and easy to be combed and styled, without the need for a further conditioning step.

The invention is also directed to the use of the combination of at least 0.01% of a cationic derivative of guar gum and at least 0.1% of an aqueous emulsion of an insoluble, non-volatile silicone, having an average particle size of less than 2 μm, both expressed in terms of the weight of the total composition, for imparting improved conditioning benefit to hair, from a shampoo composition comprising a major proportion of a surfactant.

Other Ingredients

The shampoo composition of the invention may also include minor amounts of other ingredients commonly found in shampoo compositions, such as antibacterial agents, antidandruff agents such as zinc pyridinethione or Octopirox, foam boosters, pearlescers, perfumes, dyes, colouring agents, preservatives, viscosity modifiers, proteins, polymers, buffering agents, polyols and other moisturising agents, herb extracts, mink oil or honey.

The invention is further illustrated by the following examples.

EXAMPLES

Example 1

| | % wt |
|---|---|
| Sodium lauryl ether sulphate 2EO | 16.0 |
| Lauryl betaine | 2.0 |
| Silicone oil (1) | 0.5 |
| Jaguar C13S | 0.2 |
| Carbopol 940 (2) | 0.4 |
| Preservative, colour, perfume | q.s. |
| Water | to 100.0 |

(1) Silicone oil was included as 1% of an emulsion, BY22-026 from Toray Silicone Co. Ltd. comprising

| | |
|---|---|
| Lauryl alcohol ethoxylate 2EO | 2.0 |
| Lauryl alcohol ethoxylate 21EO | 2.0 |
| Polydimethylsiloxane (60,000 cS) | 50.0 |
| Preservative | q.s |
| Water | to 100.0 |

(2) Carbopol 940 is a cross linked polyacrylate available from B F Goodrich.

The shampoo is prepared using a simple cold process whereby all the ingredients are mixed using a paddle stirrer.

The silicone particles in the emulsion have a mean particle size of 0.4 μm and remain the same size in the shampoo composition.

Example 2

| | % w/w |
|---|---|
| Sodium Lauryl ether sulphate 2EO | 16.0 |
| Cocoamidopropyl betaine | 2.0 |
| Silicone oil (1) | 4.0 |
| Jaguar C13S | 0.1 |
| Ethylene glycol distearate | 2.0 |
| Octopirox (2) | 0.5 |
| Preservative, colour, perfume | q.s. |
| Water | to 100.0 |

(1) 4.0% of emulsion BY22-026 as Example 1
(2) Piroctone olamine ex Hoechst.

The shampoo is prepared using a simple hot process whereby all the ingredients except perfume are mixed at 70° C. using a paddle stirrer. The mixture is then cooled slowly, and perfume added below 40° C.

Example 3

Several shampoos were prepared by hot mixing as in Example 2 and used in comparative tests in order to assess their conditioning properties.

All of these compositions contained

| | % wt |
|---|---|
| Sodium Lauryl ether sulphate 2EO | 16.0 |
| Cocoamidopropyl betaine | 2.0 |
| Ethylene glycol distearate | 2.0 |
| Silicone oil | 0% or 3% |
| Cationic polymer | 0% or 0.04% or 0.3% |
| Preservative, colour, perfume | q.s. |
| Water | balance to 100.0% |

In each composition the silicone oil (if any) was added as an emulsion.

Testing of the shampoo compositions was carried out using six 8 gram (20 cm) hair switches. Each is shampooed twice using 0.5 gram of shampoo each time, for a 30-second wash time, then rinsed and dried. A test shampoo was used for three switches and a control shampoo (without silicone or cationic polymer) was used for three switches.

Twelve panelists were then asked to assess the ease of combing of the dried switches, comparing test switches with control switches in a paired comparison test.

The following table sets out details of the silicone emulsions and cationic polymers used, and the test results obtained.

Panelists were asked to express a preference for the switches which were easiest to comb. The result is given as the percentage of panelists who considered the test switches easier to comb than the control switches.

| Shampoo contained | % preferring test switches | statistical significance |
|---|---|---|
| 0.3% Jaguar C13S 0% silicone | 50 | not significant |
| 0% Cationic polymer 6% silicone emulsion (1) | 57 | not significant |
| 0.3% Jaguar C13S 6% silicone emulsion (1) | 94 | better than 99.9% |
| 0.04% Jaguar C13S 6% silicone emulsion (1) | 91 | better than 99.9% |
| 0.3% Jaguar C13S 6% silicone emulsion (2) | 97 | better than 99.9% |
| 0.3% Polymer JR 400 (3) 6% silicone emulsion (1) | 64 | better than 95% |

(1) BY 22-007 from Toray Silicone Co Ltd. Contains 50% of 350 centistrokes silicone, with average particle size 0.4 μm
(2) BY 22-026 from Toray Silicone Co Ltd. Contains 50% of 60,000 centistokes silicone with average particle size 0.4 μm.
(3) Polymer JR 400 is a cationic cellulose derivative of the type described in US Pat. No. 3472480. It has a cationic charge density of 0.0013.

Example 4

Three compositions were prepared by cold mixing as in Example 1. Each composition contained

| | % wt |
|---|---|
| Sodium lauryl ether sulphate 2EO | 15.0 |
| Lauryl betaine | 6.6 |
| Coconut monoethanolamide | 1.5 |
| Ethylene glycol distearate | 1.5 |
| Jaguar C13S | 0.1 |
| Formalin | 0.15 |
| Glycerol | 1.0 |

|  | % wt |
| --- | --- |
| Silicone oil | 0% or 1% |

The ethylene glycol distearate was incorporated as a preformed paste which also contained the alkanolamide and some of the lauryl ether sulphate.

One composition contained no silicone.

Another composition contained 2% of the silicone emulsion used in Example 1, having an average silicone particle size of 0.4 μm. The third composition contained 2% of silicone emulsion prepared with the same silicone oil, but with an average particle size of 4 μm. This emulsion was prepared by emulsifying silicone oil in glycerol in the presence of sodium lauryl ether sulphate 2EO to give a preformed emulsion containing 50% silicone oil, 2% surfactant and balance glycerol. (Glycerol was added separately to the other two compositions).

The ability of the compositions to generate foam in use was tested using 8 gm (20 cm) hair switches impregnated with 0.08 gm of artificial sebum.

The switch was placed in a plastic bag, 8 ml of water at 40° C. was added, followed by 0.8 ml of the composition. The bag is held closed while the switch is massaged in the solution for 30 seconds. Then the switch was removed, squeezing it to retain all the foam in the bag. The foam was then transferred to a measuring cylinder to determine its volume.

The results obtained were:

|  | Foam volume |
| --- | --- |
| No silicone | 22.0 ml ± 3.6 ml |
| Silicone of 0.4 μm size | 22.0 ml ± 2.0 ml |
| Silicone of 4 μm size | 17.0 ml ± 2.5 ml |

Silicone of larger particle size is thus reducing foam, whereas silicone of smaller particle size, according to this invention, does not do so.

Example 5

Two compositions were prepared by cold mixing as in Example 1. Each composition contained

|  | % w/w |
| --- | --- |
| Sodium lauryl ether sulphate 2EO | 16.12 |
| Cocoamidopropyl betaine | 2.0 |
| Coconut monoethanolamide | 0.5 |
| Silicone oil | 1.0 |
| Jaguar C13S | 0.1 |
| Glycerol | 1.0 |
| Ethylene glycol distearate | 1.8 |
| Formalin | 0.1 |
| Water | to 100 |

The silicone was added as emulsions which contained 60,000 cS silicone oil. For one composition, 2% of the same emulsion as in Example 1 with an average particle size of 0.4 μm was used. For the other composition the average particle size of the silicone was 3.0 μm. This emulsion was prepared using the procedure mentioned in the previous example.

The ethylene glycol distearate was added as a preformed paste which also included the monoethanolamide, and part of the betaine and part of the ether sulphate.

Samples of the compositions were stored at 28° C., 37° C. and 50° C.

At 28° C. the sample with larger silicone particles had separated into two phases after 6 months. The sample with the smaller silicone particles did not. The composition containing larger silicone particles also separated into two layers after 2 months at 37° C. or two weeks at 50° C., whereas the composition with smaller particle size silicone did not do so.

We claim:

1. An aqueous shampoo composition comprising, in addition to water,
   (a) from 2 to 40% by weight of surfactant selected from the group consisting of anionic, nonionic, amphoteric and surfactant mixtures thereof;
   (b) from 0.01 to 3% by weight of cationic conditioning polymer which is guar hydroxypropyltrimonium chloride;
   (c) from 0.1 to 10% by weight of an insoluble, non-volatile silicone, present as emulsified particles with an average particle size of less than 2 μm.

2. A shampoo composition as claimed in claim 1 wherein the anionic surfactant is selected from the group consisting of sodium lauryl sulphate, triethanolamine lauryl sulphate, triethanolamine monolauryl phosphate, sodium lauryl ether sulphate 2EO, sodium lauryl ether sulphate 3EO, ammonium lauryl sulphate, ammonium, lauryl ether sulphate 1EO, ammonium lauryl ether sulphate 2EO, ammonium lauryl ether sulphate 3EO and mixtures thereof.

3. A shampoo composition as claimed in claim 1 wherein the amphoteric surfactant is selected from the group consisting of $C_{8-18}$ alkyl amidopropyl betaine and $C_{8-18}$ alkyl betaine.

4. A shampoo composition as claimed in claim 3 wherein the amphoteric surfactant is selected from the group consisting of lauryl betaine, cocamidopropyl betaine and sodium cocamophopropionate.

5. A shampoo composition as claimed in claim 1 wherein the insoluble, non-volatile silicone is selected from the group consisting of polyalkyl siloxanes, polyalkylaryl siloxanes and mixtures thereof.

6. A shampoo composition as claimed in claim 5 wherein the insoluble, non-volatile silicone is selected from the group consisting of polydimethyl siloxane and polymethylphenyl siloxane.

7. A shampoo composition as claimed in claim 1 wherein the silicone has an average particle size of from 0.01 to 1 μm.

8. A method of cosmetically treating hair to deposit insoluble, non-volatile silicone on the hair, which comprises washing the hair with an aqueous shampoo composition comprising:
   (a) from 2 to 40% by weight of surfactant selected from the group consisting of anionic, nonionic, amphoteric and surfactant mixtures thereof;
   (b) from 0.01 to 3% by weight of cationic conditioning polymer which is guar hydroxypropyltrimonium chloride;
   (c) from 0.1 to 10% by weight of an insoluble, non-volatile silicone, present as emulsified particles with an average particle size of less than 2μm.

9. A method of making an aqueous shampoo composition as claimed in claim 1 comprising mixing together water, the surfactant, the cationic conditioning polymer and an aqueous emulsion of the silicone, wherein the silicone in the emulsion has an average particle size of less than 2 μm.

10. A shampoo composition as claimed in claim 1 wherein the non-volatile silicone is selected from the group consisting of polyalkyl siloxanes having a viscosity from 5 to 100,000 centistokes at 25° C., polyalkylaryl siloxanes having a viscosity of from 15 to 65 centistokes at 25° C., and silicone gums consisting of polydiorganosiloxanes having a molecular weight of from 200,000 to 1,000,000.

* * * * *